(12) United States Patent
Vlak et al.

(10) Patent No.: US 6,908,616 B2
(45) Date of Patent: Jun. 21, 2005

(54) ANTIGENIC PROTEINS OF SHRIMP WHITE SPOT SYNDROME VIRUS AND USES THEREOF

(75) Inventors: Justinus Maria Vlak, Rhenen (NL); Maria Cornelia Wilhelmina Van Hulten, Wageningen (NL)

(73) Assignee: Akzo Nobel N.V., Arnhem (NL)

(*) Notice: Subject to any disclaimer, the term of this patent is extended or adjusted under 35 U.S.C. 154(b) by 50 days.

(21) Appl. No.: 10/129,806

(22) PCT Filed: Sep. 14, 2001

(86) PCT No.: PCT/EP01/10679

§ 371 (c)(1),
(2), (4) Date: Sep. 16, 2002

(87) PCT Pub. No.: WO02/22664

PCT Pub. Date: Mar. 21, 2002

(65) Prior Publication Data

US 2004/0028700 A1 Feb. 12, 2004

(30) Foreign Application Priority Data

Sep. 15, 2000 (EP) ............................................ 00203186

(51) Int. Cl.⁷ .............................................. A61K 39/12
(52) U.S. Cl. ................................ 424/204.1; 424/184.1; 424/185.1; 424/186.1; 424/817; 530/350; 536/23.72
(58) Field of Search ........................... 424/204.1, 184.1, 424/185.1, 186.1, 817; 530/350; 536/23.72

(56) References Cited

U.S. PATENT DOCUMENTS 5,834,589 A * 11/1998 Meruelo et al. ............ 530/350
5,840,535 A * 11/1998 Hillman et al. ............ 435/69.1
5,998,372 A * 12/1999 Hillman et al. ............ 514/12

OTHER PUBLICATIONS

Witteveldt et al. Protection of Penaeus monodon against White Spot Syndrome Virus by Oral Vaccination. Journal of Virology, Feb. 2004, pp. 2057–2061.*

Sequence alignment of SEQ ID No.: 2 of the instant application with SEQ ID No.: 1 of Hillman et al. (U.S. Patent Nos. 5840535 and 5998372).*

Sequence alignment of SEQ ID No.: 2 of the instant application with SEQ ID No.: 1 of Meruela et al. (U.S. Patent No. 5834589).*

* cited by examiner

Primary Examiner—James Housel
Assistant Examiner—Emily M. Le
(74) Attorney, Agent, or Firm—Mark W. Milstead

(57) ABSTRACT

The present invention relates to antigenic proteins derived from White Spot Syndrome virus having an estimated size of 19 kDa (VP 19) or 13 kDA (VP13), to the use of these proteins in vaccines and to vaccines on the basis of these proteins. Furthermore, the invention relates to antibodies against these proteins and to the use of antibodies in vaccines, to nucleic acid sequences encoding these proteins and to their use in vaccines. Also, the invention relates to the use of said proteins in the manufacture of a vaccine for prophylaxis and/or treatment of White Spot Syndrome in crustaceans, to vector vaccines and to diagnostic kits comprising said nuclei acids or antibodies.

5 Claims, 2 Drawing Sheets

ANTIGENIC PROTEINS OF SHRIMP WHITE SPOT SYNDROME VIRUS AND USES THEREOF

Figure 1:
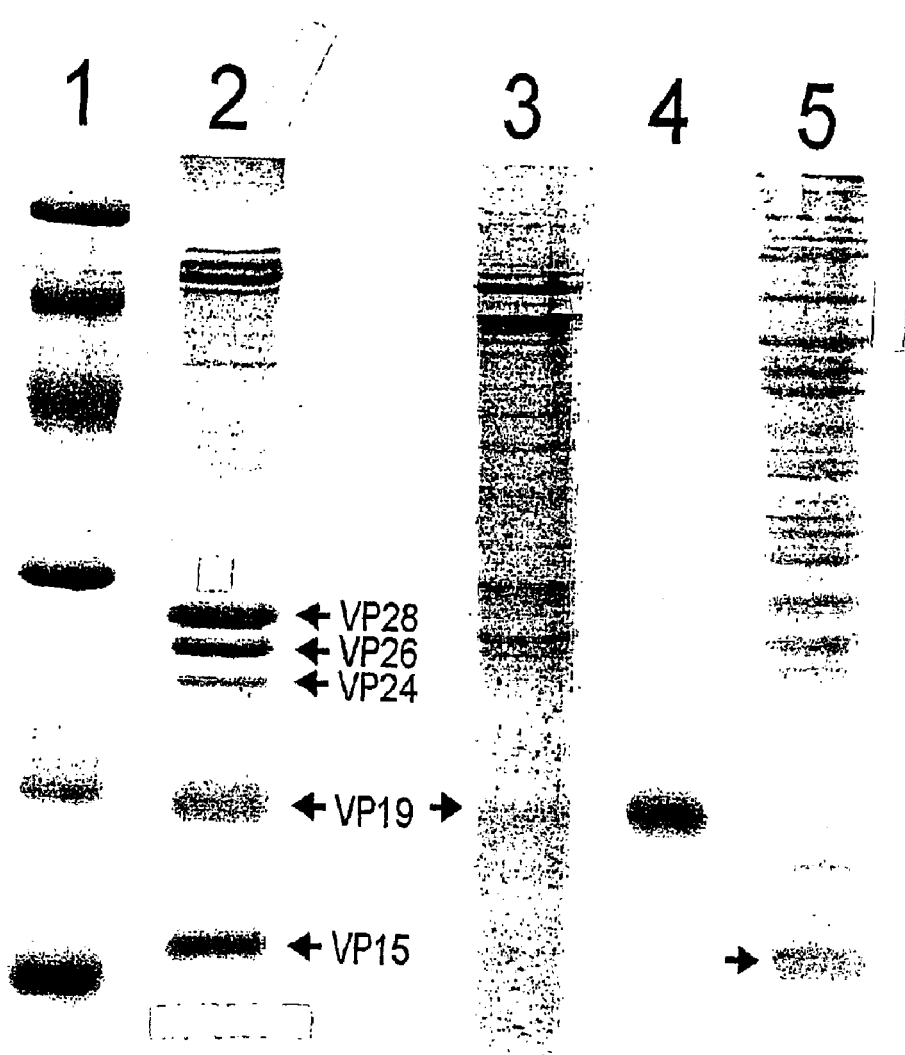

The present invention relates to antigenic proteins derived from White Spot Syndrome virus, the use of these proteins in vaccines, to vaccines on the basis of these proteins, to antibodies against the proteins, to the use of these antibodies in vaccines, nucleic acid sequences encoding them and use of said proteins in the manufacture of a vaccine for prophylaxis and/or treatment of White Spot Syndrome in crustaceans, to vector vaccines and to diagnostic kits.

White Spot Syndrome Virus (WSSV) is a major viral disease in shrimp world-wide. The virus has a wide host range among crustaceans (Flegel, 1997) and there is little genetic variation among isolates (Lo et al, 1999). Electron microscopy (EM) studies showed that the virions are enveloped and have a rod to bullet shaped appearance of about 275 nm in length and 120 nm wide with a tail-like appendage at one end. Nucleocapsids, which have lost their envelope, have a crosshatched appearance and a size of about 300 nm×70 nm (Wongteerasupaya et al., 1995). This virion morphology, its nuclear localisation and its morphogenesis are reminiscent of baculoviruses in insects (Durand et al., 1997). Originally, WSSV has been classified as an unassigned member of the Baculoviridae family (Francki et al., 1991) hence the virus has been referred to as Systemic Ectodermal Mesodermal Baculovirus (SEMBV) or White Spot Baculovirus (WSBV). At present WSSV is no longer accepted into this family (Murphy et al., 1995) due to lack of molecular information. The double stranded viral DNA has a size of well over 200 kb as derived from restriction endonuclease analysis (Yang et al., 1997).

An outbreak of WSSV in cultured shrimp causes mass mortality among shrimp. The disease is characterised by white spots on the carapace, appendages and cuticle and reddish coloration of the hepatopancreas of the shrimp. The infected shrimps show signs of lethargy and a rapid reduction in food consumption and within 3 to 5 days these shrimps die. An outbreak of WSSV leads to heavy losses in the industry of cultured shrimp and as a consequence there is a strong need for vaccines that can protect against WSSV infections. The identification and characterisation of major WSSV proteins that can be used in such a vaccine would provide the means to develop such vaccines.

Two genes have been isolated and identified as vp19 and vp13, coding for the respective proteins VP13 (13 kDa) and VP19 (19 kDa) due to their molecular weight estimated from their mobility in Coomassie Brilliant Blue-stained SDS-PAGE gels. VP19 is an envelope protein, whereas VP13 is a nucleocapsid protein. The open reading frame of vp19 comprises 366 nucleotides as shown in SEQ ID NO1 together with the deduced amino acid sequence consisting of 121 amino acids (separately depicted as SEQ ID NO 2). The open reading frame of the gene vp13 comprises at least the 186 nucleotides as depicted in SEQ ID NO 3. This ORF encodes a nucleocapsid protein VP13 comprising the amino acid sequence shown in SEQ ID $NO_4$. Two variants of protein VP13 were found, one having the amino acid sequence depicted in SEQ ID NO 4, and a longer variant having the amino acid sequence depicted in SEQ ID NO 5. The present invention provides a means to produce recombinant vaccines to protect crustaceans against infection with WSSV. The envelope protein VP19 and the nucleocapsid protein VP13 of WSSV which have been identified and characterised were found to be suitable for use in the manufacture of a subunit vaccine to protect crustaceans against infections with WSSV. The cloning and characterisation of the nucleotide sequences of the present invention provides for the production of these proteins of WSSV using recombinant technology techniques. In this way, WSSV proteins can be obtained, which are substantially free from other WSSV proteins. The isolated WSSV proteins can be used to manufacture subunit vaccines to protect crustaceans against infection of WSSV.

The proteins of the present invention are especially useful in marker vaccines. Such vaccines may comprise e.g. only VP13 and/or 19.

Alternatively the nucleotide sequences encoding the proteins of the WSSV can be used to manufacture vector vaccines to protect crustaceans against the infection with WSSV. The nucleotide sequences of the present invention can furthermore be used for diagnostic purposes, for instance to detect the presence of WSSV in the field. Additionally, the WSSV proteins of the present invention can be used to produce WSSV specific antibodies. These antibodies can be used to produce WSSV vaccines for passive immunisation of crustaceans. The antibodies can also be used for diagnostic purposes such as the detection of WSSV in crustaceans or in the field.

Thus a first embodiment of the invention provides for an antigenic protein of WSSV that is suitable for immunising crustaceans against WSSV that has an amino acid sequence that is at least 70% homologous to the amino acid sequence as depicted in SEQ ID NO: 2, SEQ ID NO: 4 or SEQ ID NO: 5 and to immunogenic fragments of said protein.

In a preferred form, the embodiment relates to such WSSV proteins that have a sequence homology of at least 80%, preferably 90%, more preferably 95% homology to the amino acid sequence as depicted in SEQ ID NO: 2, SEQ ID NO: 4 or SEQ ID NO: 5 and to immunogenic fragments of such proteins. Even more preferred is a homology level of 98% or even 100%.

The level of protein homology can be determined with the computer program "BLAST 2 SEQUENCES" by selecting sub-program: "BLASTP". A reference for this program is Tatiana A. Tatusova, Thomas L. Madden FEMS Microbiol. Letters 174: 247–250 (1999). Matrix used: "blosum62". Parameters used are the default parameters: Open gap: 11. Extension gap: 1. Gap x_ dropoff: 50.

It will be understood that, for the particular proteins embraced herein, natural variations can exist between individual WSSV strains. These variations may be demonstrated by (an) amino acid difference(s) in the overall sequence or by deletions, substitutions, insertions, inversions or additions of (an) amino acid(s) in said sequence. Amino acid substitutions which do not essentially alter biological and immunological activities, have been described, e.g. by Neurath et al in "The Proteins" Academic Press New York (1979). Amino acid replacements between related amino acids or replacements which have occurred frequently in evolution are, inter alia, Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (Science, 227, 1435–1441, 1985) and determining the functional similarity between homologous proteins. Such amino acid substitutions of the exemplary embodiments of this invention, as well as variations having deletions and/or insertions are within the scope of the invention as long as the resulting proteins are not essentially affected in their antigenic or immunogenic properties.

This explains why WSSV proteins according to the invention, when isolated from different field isolates, may have homology levels of about 70%, while still representing the same protein with the same immunological characteristics.

Those variations in the amino acid sequence of a certain protein according to the invention that still provide a protein capable of inducing an immune response against infection with WSSV or at least against the clinical manifestations of the infection are considered as "not essentially affecting the antigenic or immunogenic properties of said protein".

When a protein is used for e.g. vaccination purposes or for raising antibodies, it is however not necessary to use the whole protein. It is also possible to use a fragment of that protein that is capable, as such or coupled to a carrier such as e.g. KLH, of inducing an immune response against that protein, a so-called immunogenic fragment. An "immunogenic fragment" is understood to be a fragment of the full-length protein that still has retained its capability to induce an immune response in a vertebrate host, i.e. comprises a B- or T-cell epitope. Antibodies raised in a vertebrate host are very suitable as passive means of vaccination in shrimps. At this moment, a variety of techniques is available to easily identify DNA fragments encoding antigenic fragments (determinants). The method described by Geysen et al (Patent Application WO 84/03564, Patent Application WO 86/06487, U.S. Pat. No. NR. 4,833,092, Proc. Natl Acad. Sci. 81: 3998–4002 (1984), J. Imm. Meth. 102, 259–274 (1987), the so-called PEPSCAN method is an easy to perform, quick and well-established method for the detection of epitopes; the immunologically important regions of the protein. The method is used world-wide and as such well-known to man skilled in the art. This (empirical) method is especially suitable for the detection of B-cell epitopes. Also, given the sequence of the gene encoding any protein, computer algorithms are able to designate specific protein fragments as the immunologically important epitopes on the basis of their sequential and/or structural agreement with epitopes that are now known. The determination of these regions is based on a combination of the hydrophilicity criteria according to Hopp and Woods (Proc. Natl. Acad. Sci. 78: 38248–3828 (1981)), and the secondary structure aspects according to Chou and Fasman (Advances in Enzymology 47: 45–148 (1987) and U.S. Pat. No. 4,554, 101). T-cell epitopes can likewise be predicted from the sequence by computer with the aid of Berzofsky's amphiphilicity criterion (Science 235, 1059–1062 (1987) and U.S. patent application NTIS U.S. Ser. No. 07/005,885). A condensed overview is found in: Shan Lu on common principles: Tibtech 9: 238–242 (1991), Good et al on Malaria epitopes; Science 235: 1059–1062 (1987), Lu for a review; Vaccine 10: 3–7 (1992), Berzowsky for HIV-epitopes; The FASEB Journal 5:2412–2418 (1991).

Another embodiment of the invention relates to vaccines capable of protecting shrimp against WSSV infection, that comprise an antibody reactive with a protein or immunogenic fragment according to the invention as described above, together with a pharmaceutically acceptable carrier.

Still another embodiment of the invention relates to vaccines capable of protecting shrimp against WSSV infection, that comprise a protein or immunogenic fragment thereof according to the invention as described above together with a pharmaceutically acceptable carrier.

Still another embodiment of the invention relates to a nucleic acid sequence encoding an antigenic protein according to the invention, or an immunogenic fragment thereof. More particularly this embodiment of the invention relates to a nucleic acid sequence encoding an antigenic protein or an immunogenic fragment thereof comprising an amino acid sequence as depicted in SEQ ID No.'s 2, 4, or 5.

Preferably, the nucleic acid sequence has or comprises the sequence as depicted in SEQ ID NO 1 or 3. The respective nucleotide sequences start with the ATG codon encoding the first M residue of the deduced amino acid sequence up to the codon encoding the C-terminal amino acid residue. It must be understood that for the purpose of this invention nucleic acid sequences that have sequence homology with the sequences depicted in SEQ ID NO1 or SEQ ID NO 3 are also within the scope of the invention. The sequence homology for the purpose of this invention is considered to be at least 70%, preferably 75%, more preferably 80%, even more preferably 85%. Highly preferred are nucleic acid sequences that have sequence homology with the sequences depicted in SEQ ID NO 1 or 3 of at least 90% more preferably 95%. Homologies of 98% or even 100% are even more preferred. For the purpose of this invention sequence homology is determined by comparing the nucleotide sequence of interest with the corresponding part of the sequence depicted in SEQ ID NO 1 or 3. For the purpose of this invention the percentage sequence homology is defined as the percentage of identical nucleotides between the compared sequences.

The level of nucleotide homology can be determined with the computer program "BLAST 2 SEQUENCES" by selecting sub-program: "BLASTN". A reference for this program is Tatiana A. Tatusova, Thomas L. Madden FEMS Microbiol. Letters 174: 247–250 (1999). Parameters used are the default parameters: Reward for a match: +1. Penalty for a mismatch: −2. Open gap: 5. Extension gap: 2. Gap)_ dropoff: 50.

Nucleic acid sequences having sequence homology according to the invention can easily be isolated with one of the sequences depicted in SEQ ID NO 1 or 3 or with fragments of this sequence from closely related WSSV strains using routine cloning and hybridisation techniques. For this purpose hybridisation is carried out under stringent, preferably highly stringent conditions. Stringent hybridisation conditions are understood to be washing conditions of 1×SSC, 0.1% SDS at a temperature of 65° C.; highly stringent conditions refer to washing conditions in which the concentration SSC is being lowered towards 0.3×SSC. The specific information should not be so narrowly interpreted so as to require exclusion of erroneously identified bases. The specific sequences disclosed herein can be readily used to isolate homologous nucleotide sequences from other strains. A nucleic acid sequence that has sequence homology with one of the sequences depicted in SEQ ID NO 1 or 3 encodes a protein having an amino acid sequence which comprises alterations compared to one of the amino acid sequences depicted in SEQ ID No.'s 2, 4, or 5, whereby said alterations do not essentially affect the antigenic or immunogenic properties of said protein.

The WSSV proteins according to the invention can be obtained via standard biochemical isolation and purification methods or they can be prepared via general recombinant technology. The nucleotide sequences according to the invention are particularly suitable to be used for the recombinant production of WSSV proteins, substantially free from other WSSV proteins. The nucleotide sequences are incorporated into a suitable expression vector capable of expressing the proteins, transforming a suitable host cell with said expression vector and culturing the host cell in a suitable medium. The expressed proteins can be isolated and purified from the cells or the medium. Suitable expression vectors are, amongst others, plasmids, cosmids, viruses and YAC's (Yeast Artificial Chromosomes) which comprise the necessary control regions for replication and expression. The expression vector can be brought to expression on a host cell. Suitable host cells are, for instance, bacteria, yeast cells, insect cells and mammalian cells. Such expression techniques are well known in the art (Sambrook et al., Molecular Cloning: a Laboratory Manual, Cold Spring Harbor Laboratory Press, Cold Spring Harbor, 1989; King and Possee, 1992).

In addition, the nucleic acid sequences according to the invention can be used to manufacture a vector vaccine to vaccinate crustaceans against WSSV infections. A vector vaccine is understood to be a vaccine in which a live, attenuated bacterium or virus has been modified so that it contains one or more heterologous nucleotide sequences inserted into its genetic material. These so called vector bacteria or viruses are capable of co-expressing the heterologous proteins encoded by the inserted nucleotides. Thus in a fourth aspect the invention provides for a vector vaccine for use in prophylaxis or treatment of White Spot Syndrome in crustaceans comprising a live attenuated bacteria or virus and a pharmaceutical acceptable carrier, in which said bacteria or virus has been modified to comprise in its genetic material one or more of the nucleotide sequences of the present invention. Shrimp infected with such LRCs will produce an immunological response not only against the immunogens of the carrier, but also against the immunogenic parts of the protein(s) for which the genetic code is additionally cloned into the LRC.

As an example of bacterial LRCs, bacteria such as *Vibrio anguillarum* known in the art can attractively be used. (Singer, J. T. et al., New Developments in Marine Biotechnology, p. 303–306, Eds. Le Gal and Halvorson, Plenum Press, New York, 1998).

Also, LRC viruses may be used as a way of transporting the nucleic acid sequence into a target cell. Viruses suitable for this task are e.g. Yellow Head virus and Gill Associated virus, both belonging to the family coronaviridae.(see e.g. Spann, K. M. et al., Dis. Aquat., Org. 42: 221–225, (2000), and Cowley, J. A. et al., Dis. Aquat. Org. 36: 153–157 (1999) for the virus, or Enjuanes, L. et al., p. 28–31 of the Proceedings of the ESW, Brescia, Italia, 27–30 August 2000 for live recombinant carrier corona viruses).

The technique of in vivo homologous recombination, well-known in the art, can be used to introduce a recombinant nucleic acid sequence into the genome of a bacterium or virus of choice, capable of inducing expression of the inserted nucleic acid sequence according to the invention in the host animal.

An alternative and efficient way of vaccination is direct vaccination with DNA encoding the relevant antigen. Direct vaccination with DNA encoding proteins has been successful for many different proteins. (As reviewed in e.g. Donnelly et al., The Immunologist 2: 20–26 (1993)). This way of vaccination is attractive for the vaccination of shrimp against WSSV infection. Therefore, still another embodiment of the invention relate to vaccines comprising a pharmaceutically acceptable carrier and nucleic acid sequences encoding a protein according to the invention or immunogenic fragments thereof, or DNA fragments, e.g. plasmids, that comprise such nucleic acid sequences.

Still another embodiment of the present invention relates to a protein according to the invention for use in a vaccine.

Again another embodiment of the invention relates to the use of a protein according to the invention for the manufacturing of a vaccine for combating WSSV infections.

A vaccine according to the invention can be used to protect crustaceans such as shrimps including but not limited to members from the *Penaeidae* family such as for example *P. monodon, P. vannamei, P. chinensis, P. merguensis,* or *Metapeaeus* spp.; prawns including but not limited to members from the *Palaemonidae* family such as for example *Macrobrachium* spp. or *Palaemon* spp.; lobsters including but not limited to members from the *Palinuridae* and *Nephropidae* family such as for example *Calinectes* spp., *Palinurus* spp., *Panuliris* spp. or *Homarus* spp.; crayfish including but not limited to members from the *Astacidae* family examples of which are *Astacus* spp., *Procambarus* spp., and *Oronectes* spp.; and crab including but not limited to members from the *Cancridae* and *Portuidae* family, examples of which are *Cancer* spp., *Callinectes* spp., *Carcinus* spp. and *Portunus* spp.

A vaccine according to the invention can be prepared according to techniques well known to the skilled practitioner and described for instance in Remington's Pharmaceutical Sciences, 18$^{th}$ edition (1990), eds. A. R. Gennaro et al., chapter 72, pp. 1389–1404, Philadelphia College of Pharmacy and Science.

Vaccines according to the invention comprise an effective amount of one or more proteins, vector bacteria or virus according to the invention, and a pharmaceutical acceptable carrier. The term "effective" as used herein is defined as the amount sufficient to induce a protective response in the crustaceans. The amount of vector or protein will depend on the type of vector or protein, the route of administration, the time of administration, the species to be vaccinated as well as age, general health, temperature and diet.

In general, a dosage of 0.01 to 1000 µg protein per animal, preferably 0.5 to 500 µg, more preferably 1 to 100 µg protein per animal can be used. In case of viral vector vaccines in general a dosage of 10^3 to 10^8 pfu (plaque forming units) per animal can very efficiently be used. Bacterial vector vaccines can be given very efficiently in doses of 10^3 to 10^8 bacteria.

For DNA vaccination, amounts of DNA between 0.1 and 10 µg DNA per animal are very usefull doses.

Pharmaceutically acceptable carriers that are suitable for use in a vaccine according to the invention are sterile and physiologically compatible such as for example sterile water, saline, aqueous buffers such as alkali metal phosphates (e.g. PBS), alcohol's, polyols and the like. In addition a vaccine according to the invention may comprise other additives such as adjuvants, stabilisers, anti-oxidants, preservatives and others. Suitable adjuvants include but are not limited to aluminium salts or gels, carbomers, non-ionic block copolymers, tocopherols, monophosphoryllipid A, muramyldipeptide, oil emulsions, glucans, cytokines, saponins such as Quil A, and the like. The amount of adjuvant added depends on the nature of the adjuvant itself. Suitable stabilisers for use in a vaccine according to the invention include but are not limited to carbohydrates such as sorbitol, mannitol, starch, sucrose, dextrin, and glucose, proteins such as albumin or casein, and buffers like alkaline phosphates. Suitable preservatives include amongst others thimerosal and merthiolate. The vaccines according to the invention can be administered via injection, immersion, dipping, spray or aerosol, or per oral. Preferably the vaccine is administered to the crustaceans via immersion or per oral, especially in case of commercial aqua culture farms.

For oral administration the vaccine is preferably mixed with a suitable carrier for oral administration i.e. cellulose, food or a metabolisable substance such as alpha-cellulose or different oils of vegetable or animals origin. Particularly preferred food carriers for oral delivery of the vaccine according to the invention are live-feed organisms which are able to encapsulate the vaccine. A very suitable way of obtaining this is to feed e.g. insect cells in which a protein according to the invention has been expressed, to live-feed organisms. Suitable live-feed organisms include but are not limited to plankton-like non-selective filter feeders preferably members of Rotifera, Artemia, and the like. Highly preferred is the brine shrimp Artemia sp.

The proteins according to the invention can be used for the production of antibodies, using the general techniques available to the practitioner in the field. Preferably the proteins are used to produce specific monoclonal antibodies. Antibodies according to the invention can be prepared according to standard techniques. Procedures for immunising animals, e.g. mice with proteins and procedures for selection of hybridomas producing protein-specific monoclonal antibodies are well known in the art (see for example Cligan et al. (eds), Current protocols in Immunology 1992; Kohler and Milstein, Nature 256, pp.495–497, 1975; Steenbakkers et al., Mol. Biol. Rep. 19, pp.125–134, 1994). The obtained antibodies may be utilised in diagnostics to detect WSSV in the field or to detect the presence of WSSV in the crustaceans. The nucleotide sequences according to the invention are also suitable for use in diagnostics. Said sequences or fragments thereof can be used in for instance PCR technology to detect the presence of WSSV in the field, or in the crustaceans.

A diagnostic test for the detection of WSSV is e.g. based upon the reaction of DNA isolated from the animal to be tested, with specific probes or it is e.g. a PCR test based upon the coding sequences for the proteins according to the invention or based upon nucleic acid sequences that are complementary to those coding sequences. If nucleic acid molecules specific for the WSSV proteins according to the invention are present in the animal, these will e.g. specifically bind to specific PCR-primers and will subsequently become amplified in PCR-reaction. The PCR-reaction product can then easily be detected in DNA gel electrophoresis. PCR reactions are well-known in the art (see reference below). The nucleic acid molecules can most easily be isolated from the hepatopancreas of the animal to be tested. Standard PCR-textbooks give methods for determining the length of the primers for selective PCR-reactions with nucleic acid molecules specific for proteins according to the invention. Primers with a nucleotide sequence of at least 12 nucleotides are frequently used, but primers of more than 15, more preferably 18 nucleotides are somewhat more selective. Especially primers with a length of at least 20, preferably at least 30 nucleotides are very generally applicable. PCR-techniques are extensively described in (Dieffenbach & Dreksler, PCR primers, a laboratory manual. ISBN 0-87969-447-5 (1995)).

Nucleic acid molecules encoding a WSSV protein according to the invention or parts of those nucleic acid molecules having a length of at least 12, preferably 15, more preferably 18, even more preferably 20, 22, 25, 30, 35 or 40 nucleotides in that order of preference, wherein the nucleic acid molecules or parts hereof have at least 70% homology with the nucleic acid sequence as depicted in SEQ ID NO: 1 or 3 or a nucleic acid sequence that is complementary to nucleic acid sequence as depicted in SEQ ID NO: 1 or 3 are therefore also part of the invention. Such nucleic acid molecules can e.g. be used as primers in PCR-reactions in order to enhance the amount of nucleic acid that encodes the proteins according to the invention. This allows the quick amplification of specific nucleotide sequences for use as a diagnostic tool for e.g. the detection of WSSV in tissue as indicated above.

Another nucleic acid-based test is based upon classical hybridisation with radioactively or colour labelled protein-specific cDNA-fragments. Both PCR-reactions and hybridisation reactions are well-known in the art and are i.a. described in Maniatis/Sambrook (Sambrook, J. et al. Molecular cloning: a laboratory manual. ISBN 0-87969-309-6).

Thus, another embodiment of the invention relates to a diagnostic kit for the detection of WSSV wherein the test comprises a nucleic acid sequence that is at least 70% homologous to the nucleic acid sequence as depicted in SEQ ID NO: 1 or 3 or a nucleotide sequence that is complementary to that nucleic acid sequence, or a fragment thereof having a length of at least 12, preferably 15, more preferably 18 nucleotides.

A diagnostic test based upon the detection of antigenic material of WSSV proteins and therefore suitable for the detection of WSSV infection can e.g. also be a standard sandwich-ELISA test. In one example of such a test the walls of the wells of an ELISA plate are coated with antibodies directed against the protein according to the invention or immunogenic fragments thereof. After incubation with the material to be tested, labelled anti-WSSV antibodies are added to the wells. A colour reaction then reveals the presence of antigenic material from WSSV.

Therefore, still another embodiment of the present invention relates to a diagnostic test for the detection of WSSV, characterised in that said test comprises antibodies against a protein or an immunogenic fragment thereof according to the invention.

Thus, in another aspect, the present invention provides for a diagnostic kit comprising one or more nucleotide sequences or antibodies according to the invention. The antibodies raised against the proteins according to the invention can further be used to manufacture antibody vaccines for the passive immunisation of the crustaceans. Thus, in a further aspect, the present invention provides for a vaccine for passive immunisation against WSSV wherein the vaccine comprises antibodies raised against a protein comprising an amino acid sequence as shown in SEQ ID NO 2, SEQ ID NO 4 or SEQ ID NO 5. Such a vaccine can be prepared using standard techniques, as mentioned above. Preferably a vaccine for oral administration of the antibodies is prepared, in which the antibodies are mixed with an edible carrier such as fish food. More preferably, the vaccine is prepared from antibodies prepared in chicken eggs (IgY antibodies).

Methods for large-scale production of antibodies according, to the invention are also known in the art. Such methods rely on the cloning of (fragments of) the genetic information encoding the protein according to the invention in a filamentous phage for phage display. Such techniques are described i.a. in review papers by Cortese, R. et al., (1994) in Trends Biotechn. 12: 262–267., by Clackson, T. & Wells, J.A. (1994) in Trends Biotechn. 12:173–183, by Marks, J.D. et al., (1992) in J. Biol. Chem. 267: 16007–16010, by Winter, C. et al., (1994) in Annu. Rev. Immunol. 12: 433–455, and by Little, M. et al., (1994) Biotechn. Adv. 12: 539–555. The phages are subsequently used to screen camelid expression libraries expressing camelid heavy chain antibodies. (Muyldermafls, S. and Lauwereys, M., Journ. Molec. Recogn. 12: 131–140 (1999) and Ghahroudi, M.A. et al., FEBS Letters 414: 512–526 (1997)). Cells from the library that express the desired antibodies can be replicated and subsequently be used for large scale expression of antibodies.

REFERENCES

Durand, S., Lightner, D. V., Redman, R. M., and Bonami, J. R. (1997). Ultrastructure and morphogenesis of White Spot Syndrome Baculovirus (WSSV). *Diseases Aquat. Organisms* 29, 205–211.

Flegel, T. W. (1997). Major viral diseases of the black tiger prawn (*Penaeus monodon*) in Thailand. *World J. Microbiol. Biotechnol.* 13, 433–442.

Francki, R. I. B., Fauquet, C. M., Knudson, D. L., and Brown, F. (1991). "Classification and Nomenclature of Viruses: Fifth Report of the International Committee on Taxonomy of Viruses". Springer-Verlag, New York.

Lo, C. F., Hsu, H. C., Tsai, M. F., Ho, C. H., Peng, S. E., Kou, G. H., and Lightner, D. V. (1999). Specific genomic fragment analysis of different geographical clinical samples of shrimp white spot syndrome virus. *Diseases Aquat Organisms*.

Murphy, F. A., Fauquet, C. M., Bishop, D. H. L., Ghabrial, S. A., Jarvis, A. W., Martelli, G. P., Mayo, M. A., and Summers, M. D. (1995). "Classification and Nomenclature of Viruses: Sixth Report of the International Committee on Taxonomy of Viruses.". Virus Taxonomy Springer-Verlag, New York.

Sambrook, J., Fritsch, E. F., and Maniatis, T. (1989). "Molecular Cloning: A laboratory Manual." 2 ed. Cold Spring Harbor Laboratory, New York Wonteerasupaya, C., Vickers, J. E., Sriurairatana, S., Nash, G. L., Akarajamorn, A., Boonsaeng, V., Panyim, S., Tassanakajon, A., Withyachumnarnkul, B., and Flegel, T. W. (1995). A non-occluded, systemic baculovirus that occurs in cells of ectodermal and mesodermal origin and causes high mortality in the black tiger prawn *Penaeus monodon*. *Diseases Aquat Organisms* 21, 69–77.

Yang, F., Wang, W., Chen, R. Z., and Xu, X. (1997). A simple and efficient method for purification of prawn baculovirus DNA. *J. Virol. Meth.* 67, 1–4.

EXAMPLES

Example 1

Vaccination of *Penaeus Monodon* with WSSV Protein VP19.

Virus Stock Production

A WSSV virus stock was produced in the crayfish *Procambarus clarkii* by intramuscular injection of purified WSSV. In order to determine the dilution resulting in 90–100% mortality in the black tiger shrimp *P. monodon*, an in vivo virus titration was performed using animals of approximately 1 gram in weight. The virus stock was diluted in steps from $1 \times 10^5$ to $5 \times 10^{11}$ times in 330 mM NaCl and for each dilution 10 µl was injected intramuscularly into 10 shrimps. Shrimps that were injected with 330 mM NaCl, served as negative control for the infection. All shrimps serving as negative control (not shown) and those having received the $5 \times 10^{11}$ virus dilution survived, whereas mortality due to virus infection occurred in all groups with a lower virus dilution. Administration of virus dilutions of $1 \times 10^5$ and $1 \times 10^7$ resulted in almost 100% mortality in a period of 20 days. A delay in mortality was observed when virus dilutions of $1 \times 10^8$ and $5 \times 10^9$ were used. The $1 \times 10^8$ dilution resulted in 90% final mortality, but the time of mortality was delayed and spanned a period of 40 days. The experiment was repeated with the $1 \times 10^7$, the $1 \times 10^8$, and the $5 \times 10^9$ dilution yielding essentially the same results. The dilution of $1 \times 10^8$ was chosen as the virus dose for further experiments as this condition was expected to give the optimal response to the neutralisation in terms of mortality reduction.

Expression of WSSV Proteins VP19 and VP13 in Insect Cells

The VP19 and VP13 ORFs were expressed in insect cells using a baculovirus vector. The Bac-to-Bac system (GIBCO BRL) was used to generate recombinant baculoviruses (AcMNPV) expressing the putative WSSV virion proteins VP19 and VP13 from the baculovirus polyhedrin promoter in insect cells. Recombinant viruses were generated expressing the Green Fluorescent Protein (GFP) from the p10 promoter and each of the WSSV proteins from the baculovirus polyhedrin promoter.

Sf21 insect cells were infected with AcMNPV-WSSVvp19, and AcMNPV-WSSVvp13 with a MOI of 5 and harvested at 72 h. post infection. Extracts of infected Sf21 cells were analysed in a 15% SDS-PAGE gel (FIG. 1). Clear expression products can be observed for VP13 (FIG. 1, lane 5, and indicated here as VP15), which has the same electrophoretic mobility as its authentic counterpart in the WSSV virion (FIG. 1, lane 2). A (less clear, but clearly visible) expression product could be observed for VP19 (FIG. 1, lane 3). Therefore, a western analysis was carried out using a polyclonal antiserum raised against purified WSSV. This analysis showed that VP19 was expressed at the expected position (FIG. 1, lane 4), and hence that the vp19 ORF encoded a WSSV virion protein.

Vaccination and Challenge

The experiment was set up according to the plan in table 1. Four experimental groups were used; two control groups, the negative and positive control, one group receiving VP19 and one group receiving GFP. In the GFP group, shrimps received the same mixture that was given to the VP19 group, with the exception of VP19.

TABLE 1

Group set-up of vaccination experiment

| Group # | Group name | Vaccination | Booster | Challenge | # shrimp |
|---|---|---|---|---|---|
| 1 | Neg. control | 330 mM NaCl | 330 mM NaCl | 330 mM NaCl | 10 |
| 2 | Pos. control | 330 mM NaCl | 330 mM NaCl | WSSV | 10 |
| 3 | VP19 | VP19 | VP19 | WSSV | 10 |
| 4 | GFP | GFP | GFP | WSSV | 10 |

All groups were injected with 20 µl of their respective solutions. For the VP19 group and the GFP group a total amount of 15 µg of protein was administered for both the vaccination and booster. For dilution of the protein solutions, as well as the virus controls, a 330 mM NaCl solution was used. GFP is Green Fluorescent Protein. In the GFP group, shrimps received the same mixture that was given to the VP19 group, with the exception of VP19.

Five days after the vaccination, the shrimp were given a booster injection, two days later followed by injection of WSSV.

After the challenge, the shrimp were monitored for one week and dead shrimp were examined for the presence of WSSV by ELISA assays and electron microscopy. None of the shrimp in group 1, the negative control, died of WSSV. Group 2 shrimps started dying of WSSV infection after one and a halfway and a mortality of 100% was reached after 5 days. The first animals in vaccination groups 3 died after one and a half day, but continued slower compared to group 2. Group 3 reached 100% mortality after six days post challenge and shows a clear delay in mortality compared to the positive control. This demonstrates that vaccination of *P. monodon* shrimp with the WSSV protein VP19 has a positive effect on the survival rate of the shrimps after challenge with WSSV.

LEGEND TO THE FIGURES

FIG. 1. Lane 1 LMW Marker (Amersham pharmacia biotech), 2 SDS-PAGE gel of Purified WSSV, 3 SDS-PAGE gel of over-expressed VP19, 4 Western blot with anti-WSSV of over-expressed VP19. 5 SDS-PAGE gel of over-expressed VP13 (indicated here as VP15).

Figure 2:
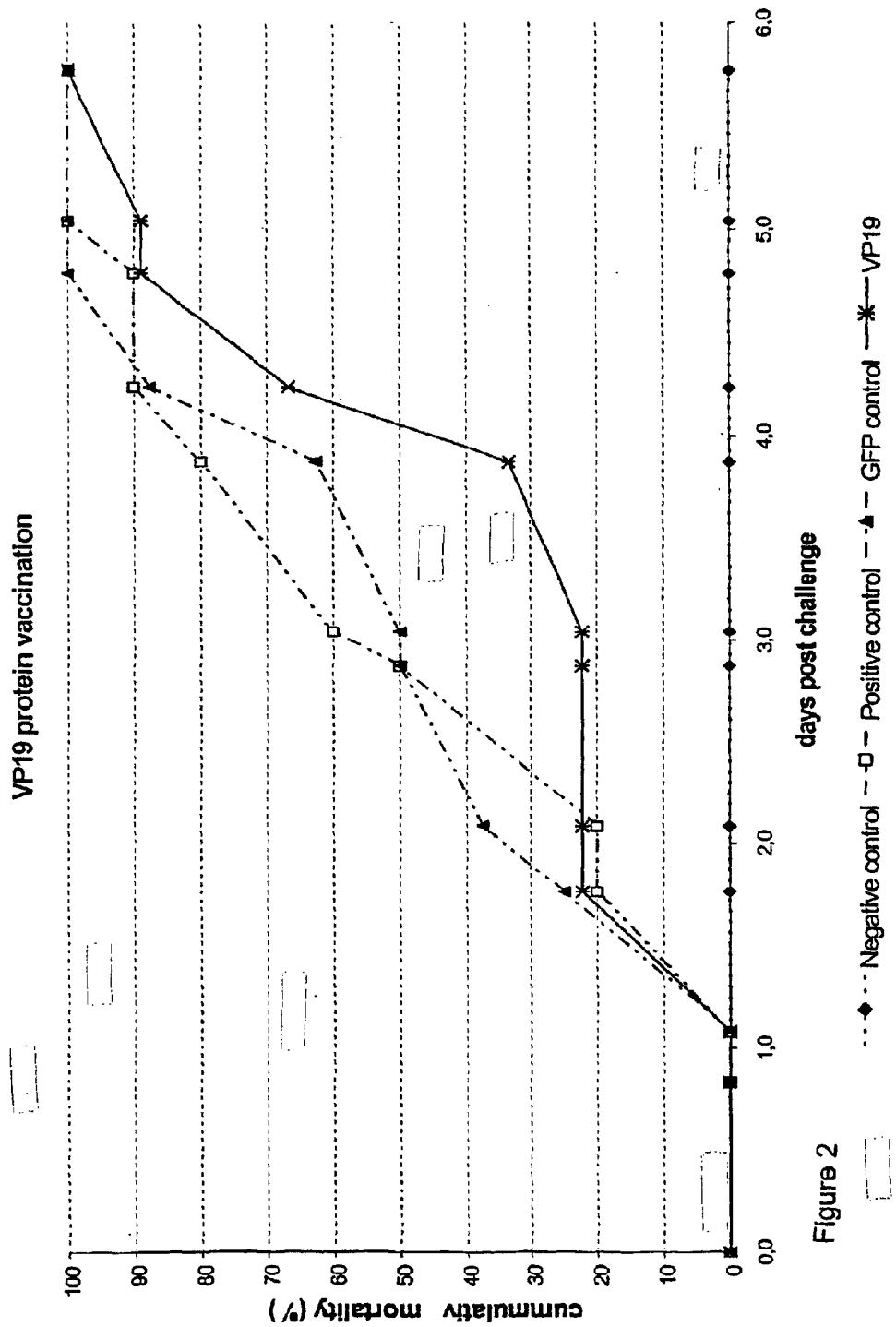

FIG. 2. This figure shows the level of effect of vaccination on mortality of shrimps after challenge with WSSV: —*—= VP19 vaccine, —♦—=negative control, —□—=positive control, —▲—=GFP control.

---

What is claimed is:

1. A composition suitable for immunizing crustaceans by injection against White Spot Syndrome Virus, WSSV, comprising:

an isolated protein consisting of an amino acid sequence represented by SEQ ID NO: 2, wherein the composition delays mortality against WSSV infectivity in crustaceans.

2. An injectable vaccine capable of delaying mortality against WSSV infectivity in crustaceans, comprising:

a composition according to claim 1, and a pharmaceutically acceptable carrier.

3. An isolated nucleic acid sequence encoding an isolated protein consisting of an amino acid sequence represented by SEQ ID NO: 2.

4. A diagnostic kit for detection of WSSV, comprising:

an isolated protein encoded by an isolated nucleic acid sequence represented by SEQ ID NO: 1.

5. An isolated protein consisting of an amino acid sequence represented by SEQ ID NO: 2.

* * * * *

SEQUENCE LISTING

<160> NUMBER OF SEQ ID NOS: 5

<210> SEQ ID NO 1
<211> LENGTH: 366
<212> TYPE: DNA
<213> ORGANISM: white spot syndrome virus
<220> FEATURE:
<221> NAME/KEY: CDS
<222> LOCATION: (1)..(366)

<400> SEQUENCE: 1

| | | | | | | | | | | | | | | | |
|---|---|---|---|---|---|---|---|---|---|---|---|---|---|---|---|
| atg | gcc | acc | acg | act | aac | act | ctt | cct | ttc | ggc | agg | acc | gga | gcc | cag | 48 |
| Met | Ala | Thr | Thr | Thr | Asn | Thr | Leu | Pro | Phe | Gly | Arg | Thr | Gly | Ala | Gln | |
| 1 | | | | 5 | | | | | 10 | | | | | 15 | | |

| gcc | gct | ggc | cct | tct | tac | acc | atg | gaa | gat | ctt | gaa | ggc | tcc | atg | tct | 96 |
|---|---|---|---|---|---|---|---|---|---|---|---|---|---|---|---|---|
| Ala | Ala | Gly | Pro | Ser | Tyr | Thr | Met | Glu | Asp | Leu | Glu | Gly | Ser | Met | Ser | |
| | | | 20 | | | | | 25 | | | | | 30 | | | |

| atg | gct | cgc | atg | ggt | ctc | ttt | ttg | atc | gtt | gct | atc | tca | att | ggt | atc | 144 |
|---|---|---|---|---|---|---|---|---|---|---|---|---|---|---|---|---|
| Met | Ala | Arg | Met | Gly | Leu | Phe | Leu | Ile | Val | Ala | Ile | Ser | Ile | Gly | Ile | |
| | | 35 | | | | | 40 | | | | | 45 | | | | |

| ctc | gtc | ctg | gcc | gtc | atg | aat | gta | tgg | atg | gga | cca | aag | aag | gac | agc | 192 |
|---|---|---|---|---|---|---|---|---|---|---|---|---|---|---|---|---|
| Leu | Val | Leu | Ala | Val | Met | Asn | Val | Trp | Met | Gly | Pro | Lys | Lys | Asp | Ser | |
| | 50 | | | | | 55 | | | | | 60 | | | | | |

| gat | tct | gac | act | gat | aag | gac | acc | gtt | gat | gat | gac | gac | act | gcc | aac | 240 |
|---|---|---|---|---|---|---|---|---|---|---|---|---|---|---|---|---|
| Asp | Ser | Asp | Thr | Asp | Lys | Asp | Thr | Val | Asp | Asp | Asp | Asp | Thr | Ala | Asn | |
| 65 | | | | | 70 | | | | | 75 | | | | | 80 | |

| gat | aac | gat | gat | gag | gac | aaa | tat | aag | aac | agg | acc | agg | gat | atg | atg | 288 |
|---|---|---|---|---|---|---|---|---|---|---|---|---|---|---|---|---|
| Asp | Asn | Asp | Asp | Glu | Asp | Lys | Tyr | Lys | Asn | Arg | Thr | Arg | Asp | Met | Met | |
| | | | | 85 | | | | | 90 | | | | | 95 | | |

| ctt | ctg | gct | ggg | tcc | gct | ctt | ctg | ttc | ctc | gtt | tcc | gcc | gcc | acc | gtt | 336 |
|---|---|---|---|---|---|---|---|---|---|---|---|---|---|---|---|---|
| Leu | Leu | Ala | Gly | Ser | Ala | Leu | Leu | Phe | Leu | Val | Ser | Ala | Ala | Thr | Val | |
| | | | 100 | | | | | 105 | | | | | 110 | | | |

| ttt | atg | tct | tac | ccc | aag | agg | agg | cag | taa | | | | | | | 366 |
|---|---|---|---|---|---|---|---|---|---|---|---|---|---|---|---|---|
| Phe | Met | Ser | Tyr | Pro | Lys | Arg | Arg | Gln | | | | | | | | |
| | | 115 | | | | | 120 | | | | | | | | | |

<210> SEQ ID NO 2
<211> LENGTH: 121
<212> TYPE: PRT
<213> ORGANISM: white spot syndrome virus

<400> SEQUENCE: 2

Met Ala Thr Thr Thr Asn Thr Leu Pro Phe Gly Arg Thr Gly Ala Gln
 1               5                  10                  15

Ala Ala Gly Pro Ser Tyr Thr Met Glu Asp Leu Glu Gly Ser Met Ser
            20                  25                  30

Met Ala Arg Met Gly Leu Phe Leu Ile Val Ala Ile Ser Ile Gly Ile
        35                  40                  45

Leu Val Leu Ala Val Met Asn Val Trp Met Gly Pro Lys Lys Asp Ser
    50                  55                  60

Asp Ser Asp Thr Asp Lys Asp Thr Val Asp Asp Asp Asp Thr Ala Asn
65                  70                  75                  80

Asp Asn Asp Asp Glu Asp Lys Tyr Lys Asn Arg Thr Arg Asp Met Met

-continued

```
                   85                  90                  95
Leu Leu Ala Gly Ser Ala Leu Leu Phe Leu Val Ser Ala Ala Thr Val
            100                 105                 110
Phe Met Ser Tyr Pro Lys Arg Arg Gln
        115                 120

<210> SEQ ID NO 3
<211> LENGTH: 186
<212> TYPE: DNA
<213> ORGANISM: white spot syndrome virus
<220> FEATURE:
<221> NAME/KEY: CDS
<222> LOCATION: (1)..(186)

<400> SEQUENCE: 3 atg gtt gcc cga agc tcc aag acc aaa tcc cgc cgt gga agc aag aag      48
Met Val Ala Arg Ser Ser Lys Thr Lys Ser Arg Arg Gly Ser Lys Lys
 1               5                  10                  15 agg tcc acc act gct gga cgc atc tcc aag cgg agg agc cca tca atg      96
Arg Ser Thr Thr Ala Gly Arg Ile Ser Lys Arg Arg Ser Pro Ser Met
            20                  25                  30 aag aag cgt gca gga aag aag agc tcc act gtc cgt cgc cgt tcc tca     144
Lys Lys Arg Ala Gly Lys Lys Ser Ser Thr Val Arg Arg Arg Ser Ser
        35                  40                  45 aag agc gga aag aag tct gga gcc cgc aag tca agg cgt taa             186
Lys Ser Gly Lys Lys Ser Gly Ala Arg Lys Ser Arg Arg
    50                  55                  60

<210> SEQ ID NO 4
<211> LENGTH: 61
<212> TYPE: PRT
<213> ORGANISM: white spot syndrome virus

<400> SEQUENCE: 4

Met Val Ala Arg Ser Ser Lys Thr Lys Ser Arg Arg Gly Ser Lys Lys
 1               5                  10                  15

Arg Ser Thr Thr Ala Gly Arg Ile Ser Lys Arg Arg Ser Pro Ser Met
            20                  25                  30

Lys Lys Arg Ala Gly Lys Lys Ser Ser Thr Val Arg Arg Arg Ser Ser
        35                  40                  45

Lys Ser Gly Lys Lys Ser Gly Ala Arg Lys Ser Arg Arg
    50                  55                  60

<210> SEQ ID NO 5
<211> LENGTH: 80
<212> TYPE: PRT
<213> ORGANISM: white spot syndrome virus

<400> SEQUENCE: 5

Met Thr Lys Tyr Pro Glu Asn Lys Arg Leu Leu Ser Arg Asn Lys Glu
 1               5                  10                  15

Thr Leu Lys Met Val Ala Arg Ser Ser Lys Thr Lys Ser Arg Arg Gly
            20                  25                  30

Ser Lys Lys Arg Ser Thr Thr Ala Gly Arg Ile Ser Lys Arg Arg Ser
        35                  40                  45

Pro Ser Met Lys Lys Arg Ala Gly Lys Lys Ser Ser Thr Val Arg Arg
    50                  55                  60

Arg Ser Ser Lys Ser Gly Lys Lys Ser Gly Ala Arg Lys Ser Arg Arg
 65                  70                  75                  80
```